(12) United States Patent
Polster

(10) Patent No.: US 11,717,437 B2
(45) Date of Patent: Aug. 8, 2023

(54) COMPRESS FOR RELIEF FROM RADIATION TREATMENTS

(71) Applicant: Natasha Polster, Long Grove, IL (US)

(72) Inventor: Natasha Polster, Long Grove, IL (US)

(*) Notice: Subject to any disclaimer, the term of this patent is extended or adjusted under 35 U.S.C. 154(b) by 780 days.

(21) Appl. No.: 16/826,262

(22) Filed: Mar. 22, 2020

(65) Prior Publication Data

US 2020/0297527 A1    Sep. 24, 2020

Related U.S. Application Data

(60) Provisional application No. 62/822,522, filed on Mar. 22, 2019.

(51) Int. Cl.
*A61F 7/10* (2006.01)
*A61F 7/00* (2006.01)
*A61F 7/02* (2006.01)

(52) U.S. Cl.
CPC ........ *A61F 7/10* (2013.01); *A61F 2007/0019* (2013.01); *A61F 2007/0217* (2013.01); *A61F 2007/0233* (2013.01); *A61F 2007/0263* (2013.01)

(58) Field of Classification Search
CPC ............... A61F 2007/0261; A61F 2007/0287
See application file for complete search history.

(56) References Cited

U.S. PATENT DOCUMENTS

| | | | |
|---|---|---|---|
| 4,802,480 A * | 2/1989 | Mader | A61F 7/0085 607/104 |
| 5,002,760 A | 3/1991 | Katzev | |
| 5,715,841 A * | 2/1998 | Utecht | A41D 19/0075 128/897 |
| 6,228,387 B1 | 5/2001 | Borod | |
| 6,342,208 B1 | 1/2002 | Hyldgaard et al. | |
| 6,348,229 B1 | 2/2002 | Eini et al. | |
| 6,792,701 B1 | 9/2004 | Ruffini et al. | |
| 7,205,012 B1 | 4/2007 | Hill | |
| 7,708,822 B2 | 5/2010 | Lahav et al. | |
| 7,977,290 B1 | 7/2011 | Deane | |
| 8,158,567 B1 | 4/2012 | Deane | |
| 8,491,940 B2 | 7/2013 | Remington et al. | |
| 8,613,961 B1 | 12/2013 | Filippova et al. | |
| 8,858,988 B2 | 10/2014 | Chamberland et al. | |

(Continued)

FOREIGN PATENT DOCUMENTS

| | | | | |
|---|---|---|---|---|
| JP | 2007332520 A | * | 12/2007 | ........... A41C 3/0064 |
| WO | WO2013103944 A1 | | 7/2013 | |

(Continued)

OTHER PUBLICATIONS

Machine Translation of JP 2007332520 A (Year: 2007).*

(Continued)

*Primary Examiner* — Kaitlyn E Smith
(74) *Attorney, Agent, or Firm* — McDonnell Boehnen Hulbert & Berghoff LLP

(57) ABSTRACT

A compress for treating and preventing radiation dermatitis, comprising a reservoir layer configured to store and release a mixture of skin-cooling ingredients, wherein the compress is cold before applying to skin exposed to radiation therapy or becomes cold after applying to skin exposed to radiation therapy.

3 Claims, 15 Drawing Sheets
(13 of 15 Drawing Sheet(s) Filed in Color)

(56) References Cited

U.S. PATENT DOCUMENTS

| | | | |
|---|---|---|---|
| 9,320,734 B2 | 4/2016 | Mahadevan et al. | |
| 2005/0226945 A1 | 10/2005 | Ruwart | |
| 2006/0243619 A1* | 11/2006 | Brown ............... | A61M 5/3205 |
| | | | 206/366 |
| 2010/0173007 A1 | 7/2010 | DiLeva | |
| 2011/0034887 A1* | 2/2011 | Forden ............... | D06M 15/333 |
| | | | 607/114 |
| 2012/0121737 A1 | 5/2012 | Vielhaber et al. | |
| 2013/0118517 A1 | 5/2013 | Foley | |
| 2014/0066837 A1 | 3/2014 | Moy | |
| 2015/0030708 A1 | 1/2015 | Chamberland et al. | |
| 2016/0113981 A1 | 4/2016 | Reaves | |
| 2019/0183672 A1* | 6/2019 | Ellerbrake-Sadler ...................... | |
| | | | A61F 13/022 |

FOREIGN PATENT DOCUMENTS

| | | |
|---|---|---|
| WO | WO2015137912 A1 | 9/2015 |
| WO | WO2015158841 A1 | 10/2015 |
| WO | WO2016090252 A1 | 6/2016 |

OTHER PUBLICATIONS

Wolf, Steven, Burns, first available online Apr. 20, 2017 (Year: 2017).*

Pereira, et al., Polymeric Films Loaded with Vitamin E and Aloe vera for Topical Application in the Treatment of Burn Wounds, Hindawi Publishing Corporation, BioMed Research Internationals, vol. 2014, Article ID 641590, 9 pages (Year: 2014).*

White, Adrian, Using Essential Oils for Burns, updated on Nov. 2, 2018 (Year: 2018).*

Gavrilovici, I., "Aloe Vera Gel Benefits for Face and Skin, Side Effects & Aloe Vera Face Masks," Beauty Ticket, Dec. 6, 2015, https://beautyticket.com/health-wellness/aloe-vera-gel-benefits-for-face-skin/.

Haddad, P. et al., "Aloe vera for prevention of radiation-induced dermatitis: a self-controlled clinical trial," Curr Oncol. Aug. 2013; 20(4): e345-e348, Accessed Jan. 10, 2017.

Oliver, K., "Lavender & Coconut Oil Moisturizer for Dry Skin," Dr. Axe, Dec. 17, 2015, https://draxe.com/beauty/moisturizer-for-dry-skin/, Accessed Jan. 10, 2017.

Salvo, N., et al. "Prophylaxis and management of acute radiation-induced skin reactions: a systematic review of the literature," Curr Oncol. Aug. 2010; 17(4): 94-112, Accessed Jan. 10, 2017.

\* cited by examiner

```
┌─────────────────────────────┐
│ Compress is premade         │
│ for the user and soaked     │
│ in soothing ingredients     │
└─────────────────────────────┘
              │
              ▼
┌─────────────────────────────┐
│ Apply cold compress         │
│ directly to skin exposed    │
│ to radiation for 10 – 30    │
│ minutes                     │
└─────────────────────────────┘
              │
              ▼
┌─────────────────────────────┐
│ Remove and discard          │
│ compress, allow skin to     │
│ dry then apply ointment     │
│ given by radiation          │
│ oncologist                  │
└─────────────────────────────┘
              │
              ▼
┌─────────────────────────────┐
│ Repeat after every          │
│ treatment, may use up       │
│ to every 2 hours or as      │
│ needed throughout and       │
│ post radiation therapy      │
└─────────────────────────────┘
```

FIG. 3

COMPRESS FOR RELIEF FROM RADIATION TREATMENTS

CROSS-REFERENCE TO RELATED APPLICATIONS

This application claims priority to U.S. Provisional Patent Application No. 62/822,522, filed Mar. 22, 2019, the disclosure of which is hereby incorporated by reference in its entirety.

BACKGROUND OF DISCLOSURE

Field

The present disclosure provides a compress comprising skin-cooling ingredients for treating and preventing radiation dermatitis, wherein the compress is cold before applying to skin exposed to radiation therapy. The temperature of the compress as well as the ingredients helps to cool the area after applying to skin exposed to radiation therapy.

Technical Background

Radiation dermatitis is a side effect of external beam ionizing radiation, which is used as a cancer treatment. Prolonged exposure to radiation treatments causes painful burns and blistering to the skin, which can begin a few days to weeks after the start of radiotherapy. More than 575,000 people undergo radiation therapy a year. Over 50% of cancer patients receive radiation therapy, making it one of the most frequently administered treatments for cancer. For breast cancer patients, this rate is even higher as 60% of these patients receive radiation therapy.

Doctors recommend salves and ointments to relieve the skin following radiation therapy. However, these salves and ointments often fail to reduce burning and blistering, especially following prolonged radiation. Ointments applied to skin that is hot due to radiation treatment can cause peeling and blistering because the ointment traps heat on the skin. Thus, there is a need for a better way to treat and prevent radiation dermatitis from radiation therapy.

As described herein, the inventor has developed a cold compress containing ingredients that cool the skin and provide relief before an ointment or a salve is applied. Surprisingly, the inventor has discovered that applying the cold compress to an area of the body that underwent radiation therapy not only lessens the degree of skin burning, but also allows heat to escape the affected area, thus improving the efficacy of ointments that are applied after the compress.

BRIEF SUMMARY OF DISCLOSURE

One aspect of the disclosure provides a compress for treating and preventing radiation dermatitis, comprising: a reservoir layer configured to store and release a mixture of skin-cooling ingredients, wherein the compress is cold before applying to skin exposed to radiation therapy or becomes cold after applying to skin exposed to radiation therapy.

In some embodiments, the mixture of skin-cooling ingredients comprises aloe vera, vitamin E, and lavender oil. In other embodiments, the mixture of skin-cooling ingredients comprises 48 parts aloe vera, 1 part vitamin E, and 0.5 part lavender oil. In yet other embodiments, the reservoir layer is soaked in a solution comprising 120 mL aloe vera, 2.5 mL vitamin E, and 1.25 mL lavender oil.

In some embodiments, the compress is refrigerated at a temperature of about 1° C. to about 4° C., or about 4° C.

In some embodiments, the reservoir layer further comprises a plastic and/or silicone backing. In other embodiments, the reservoir layer is made from a woven fabric and/or cloth. In other embodiments, the plastic and/or silicone backing causes the compress to adhere to the skin or prevent moisture from escaping from the side of the compress that is not applied to the skin.

In some embodiments, the compress can be worn under an article of clothing or held in place by an article of clothing, such as a bra, shirt, or pants.

Another aspect of the disclosure provides a method of treating or preventing radiation dermatitis in a subject in need thereof, the method comprising applying a compress to the subject's skin exposed to radiation therapy, the compress comprising a reservoir layer configured to store and release a mixture of skin-cooling ingredients, wherein the compress is cold before or after applying to the skin.

In some embodiments, the mixture of skin-cooling ingredients comprises aloe vera, vitamin E, and lavender oil. In other embodiments, the mixture of skin-cooling ingredients comprises 48 parts aloe vera, 1 part vitamin E, and 0.5 part lavender oil. In other embodiments, the compress is soaked in a solution comprising 120 mL aloe vera, 2.5 mL vitamin E, and 1.25 mL lavender oil.

In some embodiments, the compress is refrigerated at a temperature of about 1° C. to about 4° C., or about 4° C.

In some embodiments, the compress is applied to the subject's skin exposed to radiation therapy for about 2 minutes to about 20 minutes, or for about 5 minutes to about 15 minutes.

In some embodiments, the method of treating or preventing radiation dermatitis in a subject in need thereof further comprises applying ointment to the subject's skin exposed to radiation therapy after removing the compress and allowing skin to dry. In other embodiments, the compress is applied directly following radiation therapy.

In some embodiments, the compress is applied directly after treatment, then about every 2 to about every 4 hours after treatment as needed for burning sensation. In some embodiments, the treatment continues for about 4 weeks to about 8 weeks, until treatments are complete and skin heals.

In some embodiments, the subject is suffering from cancer, such as breast cancer.

Yet another aspect of the disclosure provides a method of making a compress for treating and preventing radiation dermatitis, the method comprising: (i) mixing a solution of aloe vera, vitamin E, and lavender oil; (ii) storing the solution at a temperature of about 1° C. to about 4° C. for about 1 hour to about 5 hours; and (iii) applying the cold solution to a reservoir layer of the compress until the reservoir layer is saturated.

In some embodiments, the solution comprises 48 parts aloe vera, 1 part vitamin E, and 0.5 part lavender oil. In other embodiments, the solution comprises 120 mL aloe vera, 2.5 mL vitamin E, and 1.25 mL lavender oil.

In some embodiments, the compress can be applied to skin exposed to radiation therapy about 1 minute to about 60 minutes following step (iii), or stored for days, weeks, or months at a temperature of about 1° C. to about 4° C. until it is applied to skin exposed to radiation therapy.

Yet another aspect of the disclosure provides a kit containing one or more compress for treating and preventing radiation dermatitis, wherein the compress is cold before applying to skin exposed to radiation therapy or becomes cold after applying to skin exposed to radiation therapy In some embodiments, the kit comprises about 10 to about 50 compresses.

In some embodiments, the kit comprises a container to hold the one or more compresses, wherein the container has an openable and closeable lid that is connected to a base via a hinge. In other embodiments, the kit further comprises a container to hold the one or more compresses, wherein the container is a sealed bag.

In some embodiments, the container is reusable. In other embodiments, the kit can be stored at about 1° C. to about 4° C. for about 1 hour to about 6 months.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and other features of the disclosure are explained in the following description, taken in connection with the accompanying drawings, wherein:

FIG. 1A illustrates a side view of single layer (12) compress (10). FIG. 1B illustrates a side view of a compress (10) with first (12) and second (14) layers. FIG. 1C illustrates a side view of a compress (10) with first (12), second (14), and third (16) layers. However, any number of layers is contemplated for compresses of the present disclosure.

FIG. 2A illustrates a kit (100) containing ten premade single layer compresses (10) of the present disclosure in a plastic container (112) having an openable and closeable lid (114) connected to a base (116) of the container by a hinge (118). FIG. 2B illustrates a kit (100) containing twenty premade single layer compresses (10) of the present disclosure in a plastic sealed bag container (120).

FIG. 3 is a schematic of a method of making and using a compress of the present disclosure.

FIG. 4A is an image of the skin of Patient A after 9 radiation treatments and using the compress of the present disclosure 1 time per day. FIG. 4B is an image of the treated skin of Patient A after 14 radiation treatments and using the compress of the present disclosure 1 time per day. FIG. 4C is an image of the treated skin of Patient A after 23 treatments and using the compress of the present disclosure 2 times per day beginning after the 20$^{th}$ treatment. FIG. 4D is an image of the treated skin of Patient A after completing the full course of radiation therapy, 23 treatments from a different view and with using the compress of the present disclosure 1 time per day up until the 20$^{th}$ treatment, and then 2 times per day thereafter.

FIG. 5A is an image of Patient B using two compresses for relief, one applied to the breast area and one applied to the area about the breast. FIG. 5B is an image of the skin of Patient B following 13 radiation treatments and using the compresses of the present disclosure once per day for 30 minutes at a time. FIG. 5C is an image of Patient B following 18 radiation treatments.

FIG. 6A is an image of the skin of Patient C after 1 radiation treatment. FIG. 6B is an image of the skin of Patient C after five radiation treatments. FIG. 6C is an image of the skin of Patient C after 10 radiation treatments. FIG. 6D is an image of patient C after 15 radiation treatments. FIG. 6E is an image of the skin of Patient C after 20 radiation treatments. FIG. 6F is an image of the skin of Patient C after 29 radiation treatments.

DETAILED DESCRIPTION

Figure 1A:
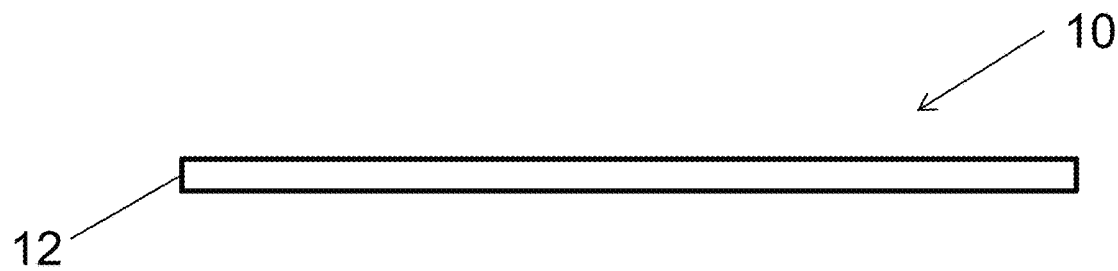
FIG. 1A-FIG. 1C are representative side views of compresses contemplated herein.

For the purposes of promoting an understanding of the principles of the present disclosure, reference will now be made to specific embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

It will be further understood that a number of aspects and embodiments are disclosed. Each of these has individual benefit and each can also be used in conjunction with one or more, or in some cases all, of the other disclosed aspects and embodiments, whether specifically delineated or not. Accordingly, for the sake of clarity, this description will refrain from repeating every possible combination of the individual aspects and embodiments in an unnecessary fashion. Nevertheless, the specification and claims should be read with the understanding that such combinations are implicitly disclosed, and are entirely within the scope of the disclosure and the claims, unless otherwise specified.

Articles "a" and "an" are used herein to refer to one or to more than one (i.e., at least one) of the grammatical object of the article. By way of example, "an element" means at least one element and can include more than one element.

As used herein, the term "and/or" includes any and all combinations of one or more of the associated listed items. It will be further understood that the use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, are expressly enumerated in this specification. These are only examples of what is specifically intended, and all possible combinations of numerical values between and including the lowest value and the highest value enumerated are to be considered to be expressly stated in this disclosure.

The term "about" in association with a numerical value means that the numerical value can vary plus or minus by 5% or less of the numerical value.

The inventor has discovered that using a compress containing a mixture of the skin-cooling ingredients described herein can lessen the degree of skin burning and allow heat to escape from the skin when applied after radiation therapy. Furthermore, the inventor has discovered that cooling the skin exposed to radiation therapy using the compress of the present disclosure improves the efficacy of ointments and salves applied thereafter. By applying ointments to skin cooled by the compress of the present disclosure instead of skin that was hot from the radiation therapy improves the efficacy of the ointments by preventing the ointments from causing blisters due to trapping heat on the skin.

One aspect of the present disclosure provides a compress for treating and preventing radiation dermatitis, wherein the compress is cold before applying to skin exposed to radiation therapy.

As used herein, the term "compress" refers to a piece of material (10) that includes a reservoir layer (12) configured to store and release a mixture of skin-cooling ingredients that can be used as a skin dressing or a wound dressing (see FIG. 1A). A compress of the present disclosure can be made from a number of materials, including but not limited to, cotton, rayon, paper towel, terry cloth, flannel, wool, polyester, polyethylene, polypropylene, microfiber cloth, bamboo fibers, hemp fibers, silicone, thermoplastics, nitrocellulose, rubber, polyamides, and the like. A compress can be made from woven and/or non-woven fabrics and/or natural and/or synthetic materials or any other appropriate material for the applications contemplated herein.

Figure 1B:
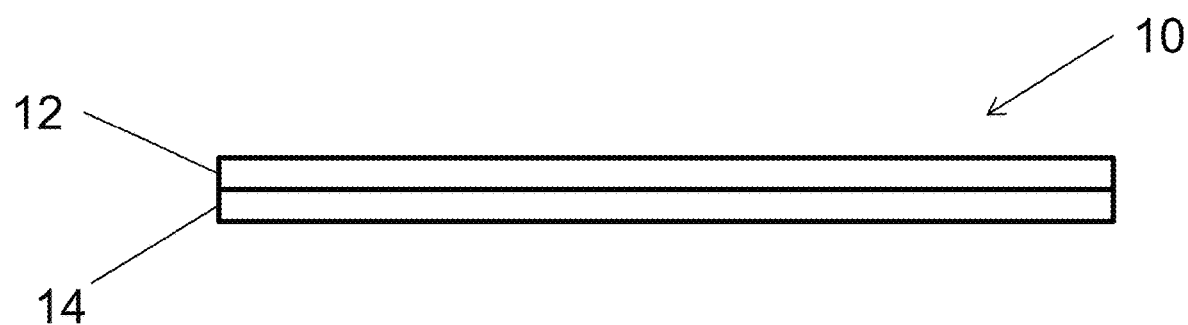
Figure 1C:
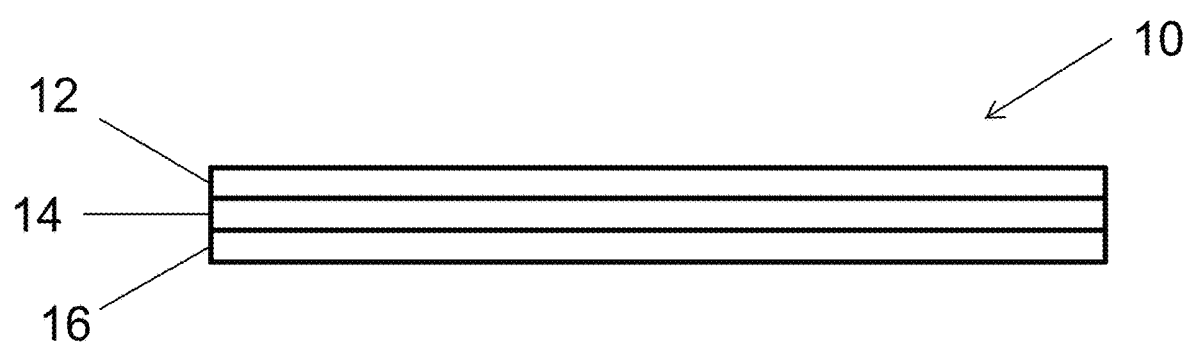

In some embodiments, the compress (10) can have two or more layers (see FIGS. 1B and 1C). For example, a compress (10) can include a reservoir layer (12) and a backing layer (14), where the backing layer comprises plastic and/or silicone or other material. In some embodiments, the backing layer can be reused with more than one compress, and is thus not permanently attached to the reservoir layer. For example, the backing layer can adhere to the moisture of the compress and then be removed once the compress has been used. In this embodiment, the backing layer can be configured to have a face (not shown) for reversible attachment to the reservoir layer that is hydrophilic to facilitate adherence to the reservoir layer when an aqueous mixture of skin-cooling ingredients is present within the reservoir layer. In another embodiment, it is contemplated that an opposite face (not shown) of the backing layer can be hydrophobic to promote removal of compresses from one another when stacked together in a package.

In other embodiments when the mixture of skin-cooling ingredients is oil-based, the surface of the backing layer can be oleophilic to facilitate adherence. In another embodiment, it is contemplated that an opposite face (not shown) of the backing layer can be hydrophilic to promote removal of compresses from one another when stacked together in a package.

In other embodiments, it is contemplated that a compress (10) can include a reservoir layer (12) and a backing layer (14), wherein the backing layer (14) is permanently attached.

In some embodiments, the plastic or silicone backing prevents moisture from escaping from the side of the compress that is not applied to the skin. Such embodiment can help protect a user's clothing when the compress is worn under clothing.

In other embodiments, the plastic or silicone backing contains an adhesive strip (not shown) that causes the backing of the compress to adhere to skin that has not been exposed to radiation therapy (e.g. opposite of the irradiated skin) to position the side of the compress containing ingredients on skin that has been exposed to radiation therapy. For example, the backing of the compress can adhere to the inside of an arm close to an armpit (e.g., the right arm) such that reservoir layer (12) of the compress (10) containing the skin-cooling ingredients can be applied to skin on the side of a breast that touches the arm (e.g., the right breast), and can be held in place by means of keeping the arm next to the body. In such embodiments, the adhesive strip is positioned on a side opposite of the reservoir layer with the adherent oriented away from the reservoir layer. In another embodiment, the adhesive strip can be included as part of the backing layer such that the strip adheres the compress to skin adjacent the irradiated site, similar to a conventional adherent bandage. In some embodiments, the adherent layer can be protected prior to use by an optional peelable layer (not shown).

In some embodiments, the compress (10) can have an additional layer (16) that can contain chemicals that can cause an endothermic reaction within the additional layer. Similarly, the backing layer (14) can be similarly configured to contain chemicals that can cause an endothermic reaction to cool the compress when triggered by mixing or some other means. Such embodiments are referred to herein as "self-cooling compresses."

In some embodiments, the compress can be worn under an article of clothing. In other embodiments, the compress can be applied to an area of skin exposed to radiation therapy and held in place by an article of clothing (e.g., bra, shirt, pants, undergarments, or any article containing an elastic band). Thus, the compress described herein can allow the patient to use it under their clothing for portability as well as a way to protect their clothing.

The compress of the present disclosure can be a variety of sizes and shapes and can be adjusted (e.g., by cutting or tearing the compress material) to cover an area of skin that has been exposed to radiation therapy. For example, the compress can be in the shape of a rectangle, square, circle, oval, or a non-symmetrical shape that is made to fit the pattern of irritated or burned skin following radiation therapy. The size of the compress can be about 4 inches by 4 inches, 4 inches by 5 inches, 4 inches by 6 inches, 4 inches by 7 inches, 5 inches by 4 inches, 5 inches by 5 inches, 5 inches by 6 inches, 5 inches by 7 inches, 5 inches by 8 inches, 6 inches by 5 inches, 6 inches by 6 inches, 6 inches by 7 inches, 6 inches by 8 inches, or 6 inches by 9 inches, 7 inches by 7 inches, 7 inches by 8 inches, 8 inches by 8 inches, 8 inches by 10 inches, or 10 inches by 10 inches. The compress can also have a diameter of about 3 inches, 4 inches, 5 inches, or 6 inches, or more. Any size and shape of compress is contemplated herein.

The compress of the present disclosure can comprise a mixture of skin-cooling ingredients. The term "skin-cooling ingredients" as used herein refers to ingredients that can cool (e.g., allow heat to escape or feel cool to the touch), soothe, and bring relief to skin that has been exposed to radiation therapy. Skin-cooling ingredients include, but are not limited to, aloe vera leaf extract (e.g., aloe vera gel or aloe vera juice), vitamin A oil, vitamin C oil, vitamin E oil, vitamin B1 oil, vitamin B3 oil, vitamin B6 oil, vitamin B12 oil, lavender oil, peppermint oil, coconut oil, tea tree oil, calendula oil, geranium oil, helichrysum oil, chamomile oil, eucalyptus oil, mineral oil, almond oil, olive oil, and/or combinations thereof.

Additional contemplated ingredients include topical analgesics.

In some embodiments, the skin-cooling ingredients comprise a mixture of aloe vera juice, vitamin E, and lavender oil. In other embodiments, the compress comprises 48 parts aloe vera juice, 1 part vitamin E, and 0.5 parts lavender oil. In other embodiments, the compress comprises a solution comprising 120 mL aloe vera juice, 2.5 mL vitamin E, and 1.25 mL lavender oil.

In some embodiments, the compress does not contain any preservative ingredients (e.g., methylisothiazolinone, benzyl alcohol, or bronopol).

The compress of the present disclosure is cold at the time that it is applied to skin exposed to radiation therapy. The compress can become cold, for example, by applying a refrigerated solution containing skin-cooling ingredients to a compress material that is at room temperature, or by means of storing the entire compress saturated with a skin-cooling solution at a refrigerated temperature and removing the compress from the refrigerated environment (e.g., a refrigerator or cooler) immediately prior to use. In other embodiments, the compress can be saturated with the skin-cooling ingredients, stored at room temperature, and then placed in a refrigerated environment before use.

In some embodiments, the skin-cooling ingredients are mixed and then refrigerated at a temperature of about 1° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., or 4.5° C. In some embodiments, the skin-cooling ingredients are mixed and then refrigerated at a temperature of about 1° C. to about 4.0° C. In other embodiments, the skin-cooling ingredients are mixed and then refrigerated at a temperature of about 4.0° C.

The mixture containing the skin-cooling ingredients can be refrigerated for about 10 minutes, 15 minutes, 30 minutes, 1 hour, 2 hours, 3 hours, 5 hours, 10 hours, 15 hours, 24 hours or until the solution uniformly reaches the desired temperature (e.g., 4.0° C.). A person of ordinary skill in the art would appreciate that the time that the mixture containing the skin-cooling ingredients is cooled before use will depend on the volume of the solution and desired temperature of the solution.

In embodiments where the compress is self-cooling, a user can trigger/activate the cooling layer and apply direct to the affected area directly.

Once the mixture containing the skin-cooling ingredients is prepared, it can be stored at any of the temperatures described herein for days, weeks, months or years. In some embodiments, the compress containing the skin-cooling ingredients can be stored at about 1° C. to about 4.0° C. for about sixth months before use.

The solution of skin-cooling ingredients can be applied to the compress until the compress is saturated with the solution. Saturation means that the compress is uniformly moist with the solution such that the solution can transfer to the skin when the compress is applied to skin. The solution comprising the skin-cooling ingredients can be applied to the compress, for example, by pouring the solution directly onto the compress or by soaking the compress in a container containing the solution.

The term "radiation dermatitis," also known as radiodermatitis or x-ray dermatitis, refers to damage to the outer layers of the skin caused by radiation therapy. Signs of radiation dermatitis can include redness, skin swelling and edema, skin peeling, skin dryness, skin burning, skin thinning, and skin blisters or ulcers. The severity of radiation dermatitis can vary from mild redness, itchiness, and irritation to painful, broken skin that is susceptible to infection. Radiation-induced dermatitis can occur after the $5^{th}$ to $7^{th}$ radiation treatment or earlier in some patients. Radiation dermatitis can sometimes not develop for weeks, months, or even years after completing radiation therapy.

In some embodiments of the present disclosure, the skin is exposed to radiation therapy as part of a treatment for cancer (e.g., breast cancer). Radiation therapy can be used on many parts of the body to treat a variety of cancers. For example, radiation therapy can be used to treat cancers of the head, neck, breast, cervix, prostate, and eye. The skin of the head, neck, face, ears, chest, arms, under arms, breast, stomach, hips, legs, and back can be impacted by radiation therapy and can be susceptible to developing radiation dermatitis. The compress of the present disclosure can be applied to skin on any part of the body exposed to radiation therapy.

Another aspect of the present disclosure provides a method of treating or preventing radiation dermatitis in a subject in need thereof, the method comprising applying a compress containing skin-cooling ingredients to skin exposed to radiation therapy, wherein the compress is cold or triggered to cool before applying to the skin.

As used herein, the terms "treating" and "treatment" are used interchangeably to refer to both therapeutic treatment and prophylactic or preventative measures. It refers to curing, attenuating, alleviating, minimizing, or suppressing the harmful effects of a complication or symptom of a treatment (e.g., radiation dermatitis and any of the symptoms associated with radiation dermatitis).

As used herein, the terms "preventing" and "prevention" are used interchangeably to refer to impeding, delaying, halting, or reversing the progression of a complication or symptom of a treatment (e.g., radiation dermatitis and any of the symptoms associated with radiation dermatitis). For example, preventing radiation dermatitis can mean that the skin exposed to radiation therapy does not burn, blister, peel, swell, thin, or become severely red and painful over the course of treatment or the skin burns, blisters, peels, swells, thins, or reddens to a lesser degree over the course of radiation therapy as compared to the skin of a patient who did not use the compress during radiation therapy.

As used herein, the terms "subject" includes human and non-human animals. Exemplary human subjects include a human patient suffering from cancer (e.g., breast cancer) that is undergoing radiation therapy. The term "non-human animals" includes all vertebrates, e.g., non-mammals (such as chickens, amphibians, reptiles) and mammals, such as non-human primates, domesticated and/or agriculturally useful animals (such as sheep, dogs, cats, rabbits, cows, pigs, etc.), and rodents (such as mice, rats, hamsters, guinea pigs, etc.). The compresses and methods described herein can also be used for veterinary purposes to treat and/or prevent radiation dermatitis in non-human animals undergoing radiation therapy. The side effects of radiation therapy in non-animals are similar to the side effects experienced in humans.

In some embodiments, the compress is applied to the skin exposed to radiation therapy for about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 25 minutes, 30 minutes, or 1 hour. In some embodiments, the compress is applied to the skin exposed to radiation therapy for about 2 minutes to about 20 minutes. In other embodiments, the compress is applied to the skin exposed to radiation therapy for about 5 minutes to about 15 minutes.

The method described herein can further comprise applying an ointment, cream, balm, salve, or moisturizer (e.g., any ointment prescribed or recommended by a physician following radiation therapy or any over the counter topical products for soothing skin burns) after removing the compress and allowing skin to dry. The cold compress cools the skin so that when an ointment is applied, the heat is not trapped to cause more irritation or blistering.

In some embodiments, the compress is applied directly following radiation therapy (e.g., within seconds, minutes, or hours).

In some embodiments, the compress can be applied about every 2 hours, every three hours, every 4 hours, every 5 hours, every 6 hours, every 8 hours, every 12 hours, or every 24 hours after radiation therapy for the duration of the treatment, which can last, for example, for about 3 weeks to about 9 weeks. In some embodiments, the compress can be applied directly after treatment, then about every 2 to about every 4 hours after treatment as needed for burning sensation. In some embodiments, the treatment continues for about 4 weeks to about 8 weeks, until treatments are complete and skin heals. The compress described herein can be used anytime in between treatments, or after treatments have concluded, as needed for burn relief, making enduring radiation therapy more comfortable for the subject.

In some embodiments, more than one compress (e.g., 2, 3, 4, 5, or 6 or more compresses) can be applied at the same time to an entire area that is exposed to radiation therapy. The one or more compresses can be applied adjacent to each other where the edges of the compresses touch or overlap. For example, for a patient undergoing radiation therapy to the breast, one or more compresses can be used to cover the skin on the breast area, one or more compresses can be used to cover the skin in the area above or below the breast, and one or more compresses can be used to cover the skin in the underarm area adjacent to the breast area being treated with radiation therapy.

Another aspect of the present disclosure provides a method of making a compress for treating and preventing radiation dermatitis, the method comprising: (i) mixing a solution of skin-cooking ingredients (e.g., aloe vera, vitamin E, and lavender oil); (ii) storing the solution at a temperature of about 1° C. to about 4° C. for about 1 hour to about 5 hours; and (iii) applying the solution to the compress until the compress is saturated.

In some embodiments, the compress can be applied to skin exposed to radiation therapy about 1 minute to about 60 minutes following step (iii), or stored for days, weeks, or months at a temperature of about 1° C. to about 4° C. until it is applied to skin exposed to radiation therapy.

Figure 2A:
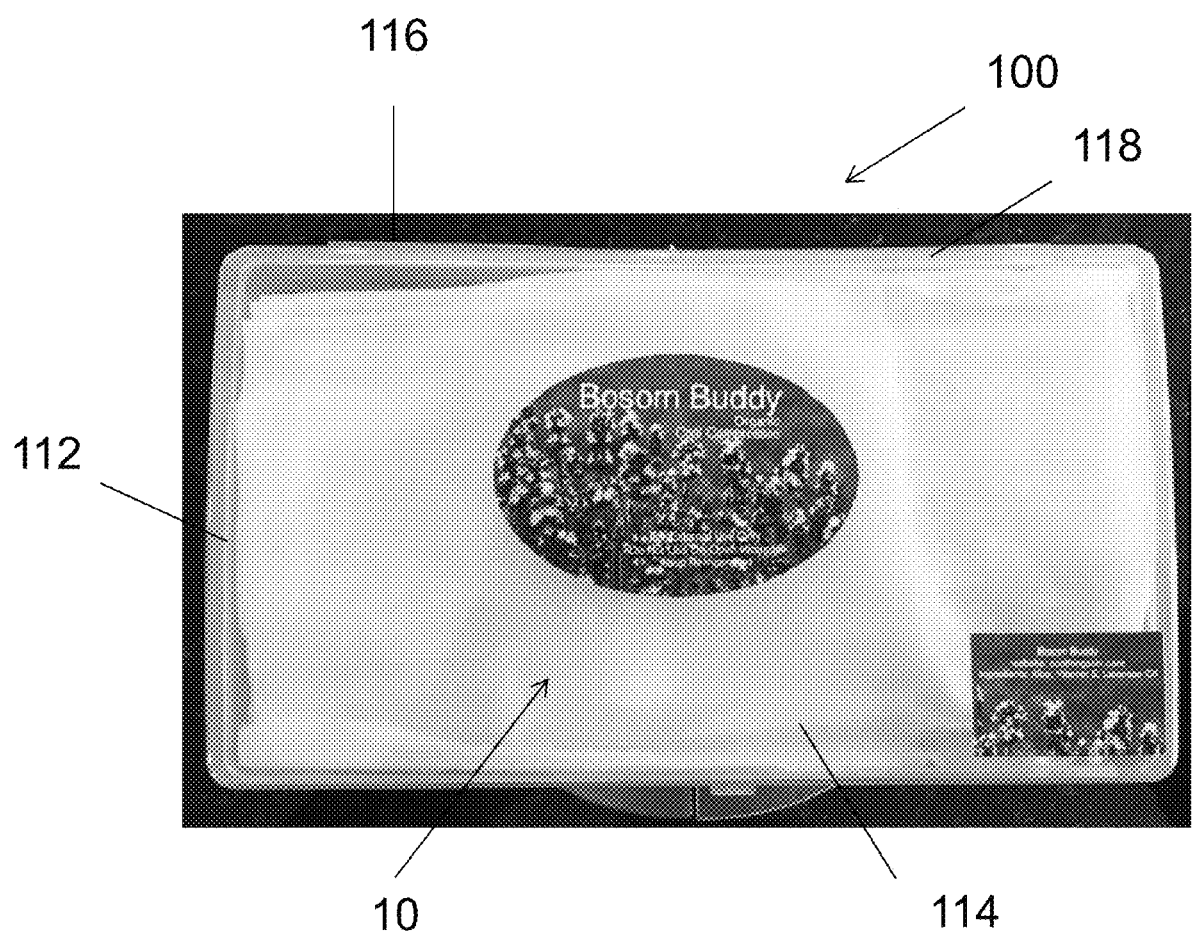
FIG. 2A-FIG. 2B are representative views of kits containing a plurality of compresses (10) contemplated herein.
Figure 2B:
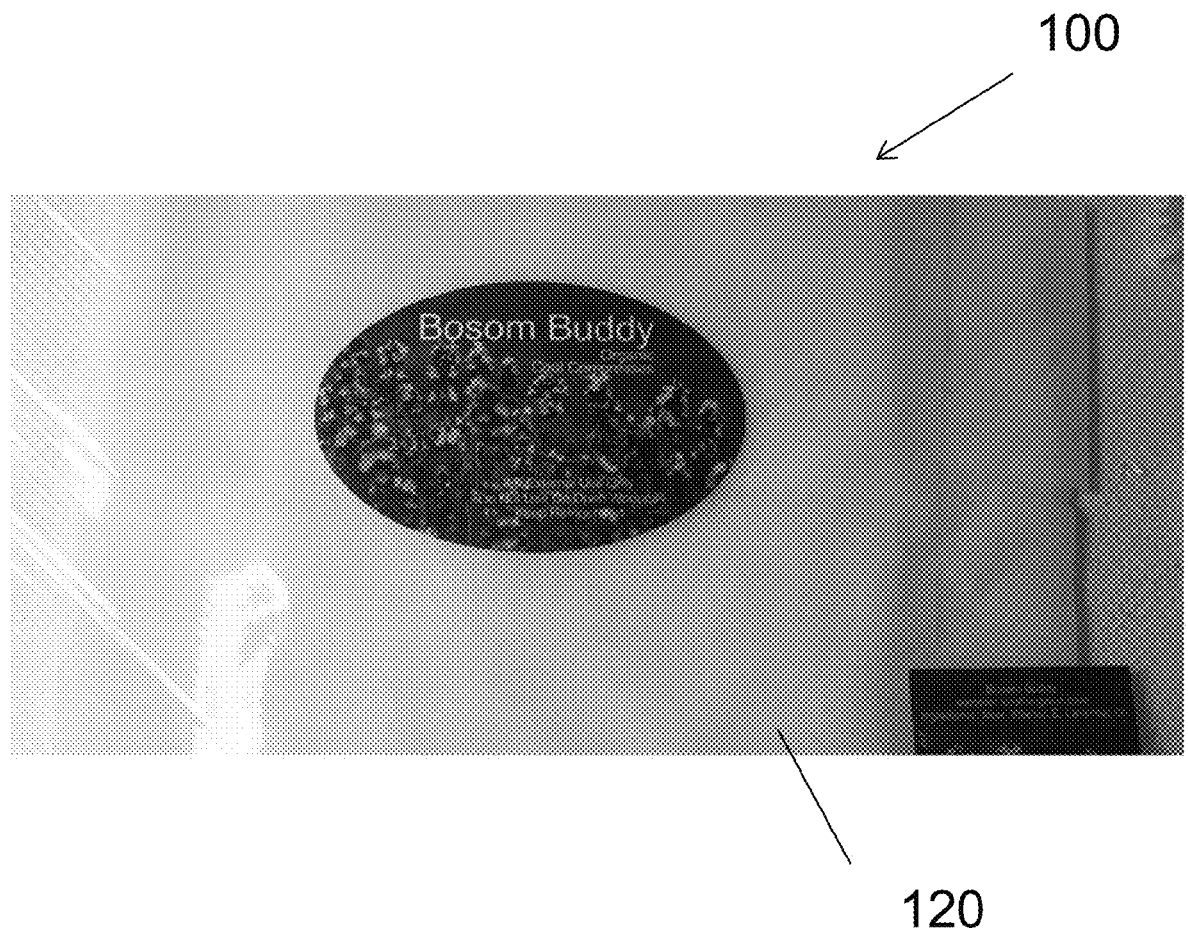

Another aspect of the present disclosure is shown in FIG. 2A and FIG. 2B which provides a kit (100) comprising one or more compresses (10) for treating and preventing radiation dermatitis, wherein the compress is cold before applying to skin exposed to radiation therapy or becomes cold after applying to skin exposed to radiation therapy.

In some embodiments, the kit comprises about 10, 15, 20, 30, 35, 40, 45, 50, 55, 60, 65, 70, 75, 80, 85, 90, 95, or 100 or more compresses.

In some embodiments, the kit (100) comprises a container (112) to hold the one or more compresses (10). The container (112) can have an openable and closeable lid (114) that is connected to a base (116) of the container by a hinge (118). The kit 100 can also include a sealed bag (120, see FIG. 2B). The containers (112 and 120) of the kits described herein can be made from a variety of plastic or plastic-like materials (e.g., Polyethylene Terephthalate (PETE or PET), High-Density Polyethylene (HDPE), Polyvinyl Chloride (PVC), Low-Density Polyethylene (LDPE), Polypropylene (PP), or Polystyrene or Styrofoam (PS)), or any other material that can create an airtight closure and be stored at about 1° C. to about 4° C.

The containers (112 and 120) of the kit (100) described herein can be in the shape of a rectangle, square, oval, circle, or any shape or size such that they are large enough to contain a compress of the disclosure.

In some embodiments, the containers (112, 120) of the kit (100) are reusable. For example, once the compresses 10 contained in the kit 100 are used, new compresses that are contained in a sealed bag (120) can be removed from the bag and placed in the container (112) for later use. In one embodiment, the bag (120) can include a closure (not shown) such as a zipper, an adhesive strip, and the like to permit a user to access compresses 10 within the bag and replenish the container 112 with additional compresses 10 and reseal the bag to store the remaining compresses within the bag in an airtight and watertight container.

In some embodiments, the kit can be stored at about 1° C. to about 4° C. for days, weeks, months, or years. In other embodiments, the kit can be stored at room temperature and then placed in an environment of about 1° C. to about 4° C. prior to use.

The following examples are offered by way of illustration and not by way of limitation.

Example 1: Compress for Skin Exposed to Radiation Therapy

A compress (10) was prepared by mixing a solution of skin-cooling ingredients (120 ml Organic Aloe Vera Juice, 2.5 ml Vitamin E Oil, and 1.25 ml Lavender Oil) in a 4 ounce amber bottle, shaking the mixture in the bottle until the ingredients were homogenous, refrigerating the solution at 4° C. for about 2 hours or until the solution reached a temperature of 4° C., shaking well and then applying the mixture to a paper towel or cloth of about 5 inches by 5 inches. Once the compress was saturated with the skin-cooling mixture, the compress was applied to an area of skin that had been exposed to radiation therapy.

Ten other compresses were prepared and stored in a container at 4° C. for later use (FIG. 2A).

The size of the compress was large enough to cover the entire area of skin that was exposed to radiation therapy, and was applied to the skin for about 5 minutes to 15 minutes. The compress was covered with a piece of plastic wrap or a reusable plastic shield to protect clothing from moisture. The compress was kept in place for the breast patients by securing it under a bra. After removing and discarding the compress, the skin was allowed to dry, and ointment prescribed by the radiation oncologist was applied to the cooled skin (FIG. 3). This process was repeated with a fresh compress as needed up to every 2 hours for relief of painful skin throughout the radiation treatments and until the skin was healed following the completion of the treatments. The solution was kept under refrigeration and the compresses were used following every radiation treatment and until the skin was healed once radiation treatments were concluded.

Multiple single-use compresses can be prepared using this method. Likewise, the skin cooling mixture can be scaled up to larger volumes having a mixture of 48 parts Aloe Vera Juice, 1 part Vitamin E Oil, and 0.5 part Lavender Oil. The compresses can then be stored in a refrigerator until they are ready to be used and up to about 6 months after preparation.

Example 2: Compress with Backing for Skin Exposed to Radiation Therapy

A compress is prepared by mixing a solution of skin cooling ingredients in a 4 ounce amber bottle, shaking the mixture in the bottle until the ingredients are homogenous, refrigerating the solution at 4° C. or until cold and storing under refrigeration, applying the mixture to a paper towel or cloth to create the compress, and applying a plastic or silicone backing that is of the same or similar dimensions of the compress to one side of the compress. The plastic or silicone backing adheres to the compress from the moisture of the solution saturated in the cloth. The plastic or silicone backing can be reused.

The compress is immediately applied cloth side down to cover an entire area of skin that had been exposed to radiation therapy or stored in the refrigerator until it is used up to 6 months after preparation. The compress is held in place on the irradiated skin using a clothing article (e.g., a bra). The plastic or silicone backing keeps clothing dry.

The compress is applied to the skin for about 5 to about 15 minutes. The compress is then removed and discarded, the skin is allowed to dry, and the patient can apply a moisturizing ointment to the cooled irradiated skin area. Compress application can be repeated as needed up to every 2 hours for relief of painful skin and continue throughout the radiation treatments and until skin is healed following the completion of the treatments.

Example 3: Skin Cooling Compress to Treat Radiation Dermatitis

To determine whether the skin cooling compress could treat and prevent radiation burns, a compress made according to Example 1 was applied to the skin of three patients: Patient A, Patient B, and Patient C. Patients A and B received radiation therapy to the breast area, and Patient C received radiation therapy to the neck area. As a control, Patient D received radiation therapy to the neck area but did not use a compress at any point during treatment.

Patient A

Patient A used the compress following exposure to radiation therapy as part of treatment for breast cancer over the entire course of radiation therapy, with the compress being applied to the treated skin once per day up until the 20$^{th}$ treatment, and then twice per day thereafter. Patient A also applied ointment that was prescribed by a radiation oncologist each time after the compress was removed.

Figure 4A:
FIG. 4A-FIG. 4D illustrate an area of treated skin of Patient A over the course of radiation treatments using the compress of the present disclosure.
Figure 4B:
Figure 4C:
Figure 4D:
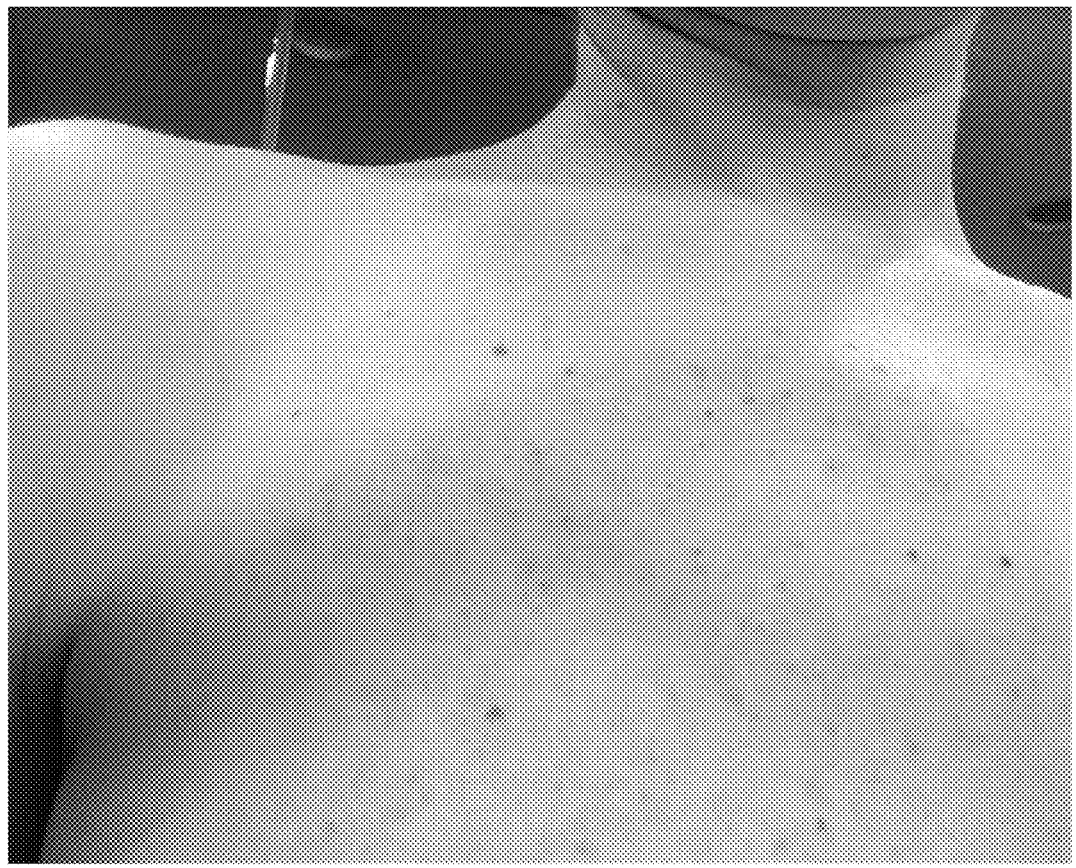

After 9 radiation treatments using the compress once per day following the treatment, Patient A had not developed radiation dermatitis (FIG. 4A). After 14 radiation treatments using the compress once per day following the treatment, Patient A had not developed radiation dermatitis (FIG. 4B). After 23 treatments using the compress of the present disclosure 2 times per day beginning after the 20$^{th}$ treatment, Patient A had not developed radiation dermatitis (FIG. 4C). At the end of the full course of radiation treatments, with using the compress, Patient A's skin never burned nor peeled and was healing well (FIG. 4D).

Patient B

Figure 5A:
FIG. 5A-FIG. 5C illustrate an area of treated skin of Patient B over the course of 20 radiation treatments and using the compress of the present disclosure on the breast area once per day for 30 minutes at a time beginning after 8 radiation treatments. After 9 radiation treatments, the patient began to notice skin above the breast area was getting red and began using two compresses to cover both the breast area and the area above the breast.
Figure 5B:
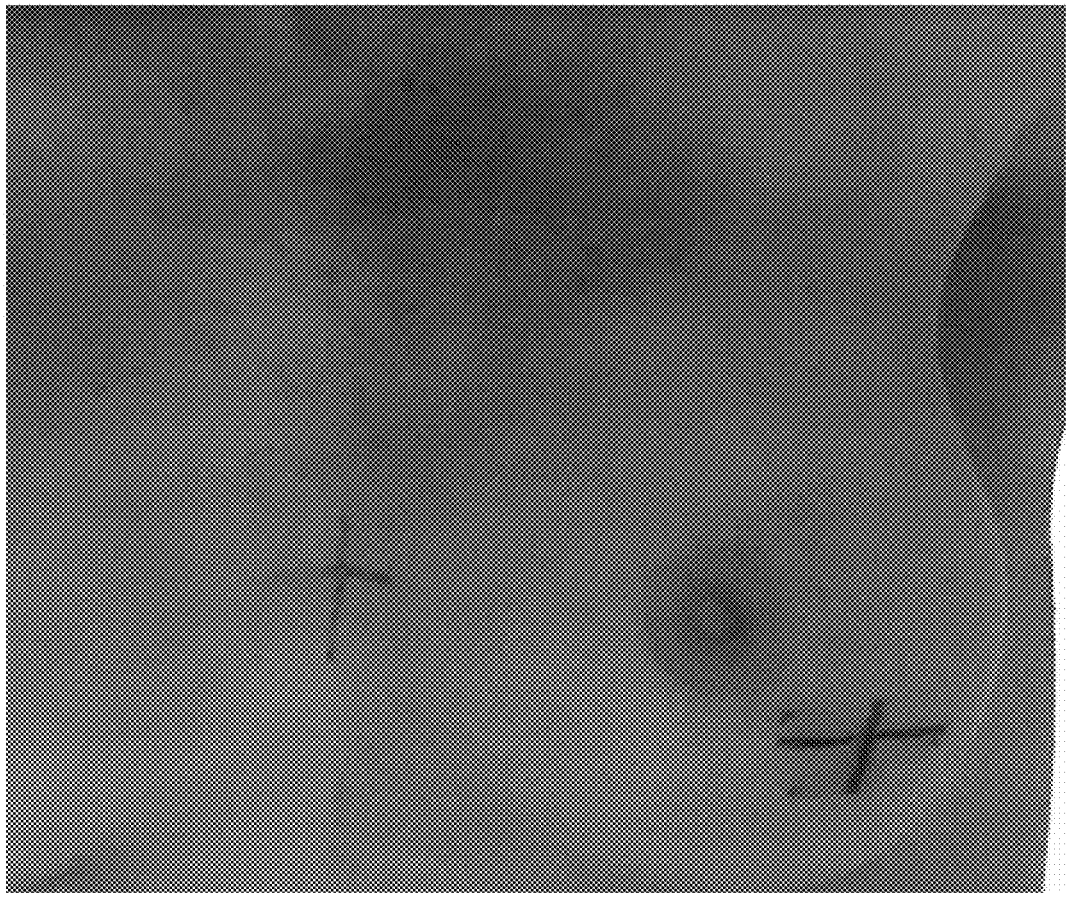
Figure 5C:

Patient B received 20 radiation treatments to the breast area as part of a treatment for breast cancer. Patient B used the compress(es) for 30 minutes following each treatment. After the compress was removed and the skin cooled, Patient B applied Aquaphor® to the area of skin exposed to radiation therapy. Patient B used the compress only on the breast area for first 8 treatments. The breast area did not turn red when using the compress. After treatment 9, Patient B began to notice the skin above the breast area was getting red and began using two compresses to cover both breast area and above the breast for the course of the remaining treatments (FIG. 5A). After 13 treatments, the skin above the breast area had mild redness, however the breast area did not turn red (FIG. 5B). The same is true after 18 radiation treatments (FIG. 5C).

The nurses commented several times how well Patient B's skin was doing. Patient B never applied the compress to the underarm area.

Patient C

Figure 6A:
FIG. 6A-FIG. 6F illustrate an area of treated skin of Patient C receiving 35 radiation treatments to the neck area and using a compress of the present disclosure once per day, immediately following treatment, over the entire course of radiation treatments.
Figure 6B:
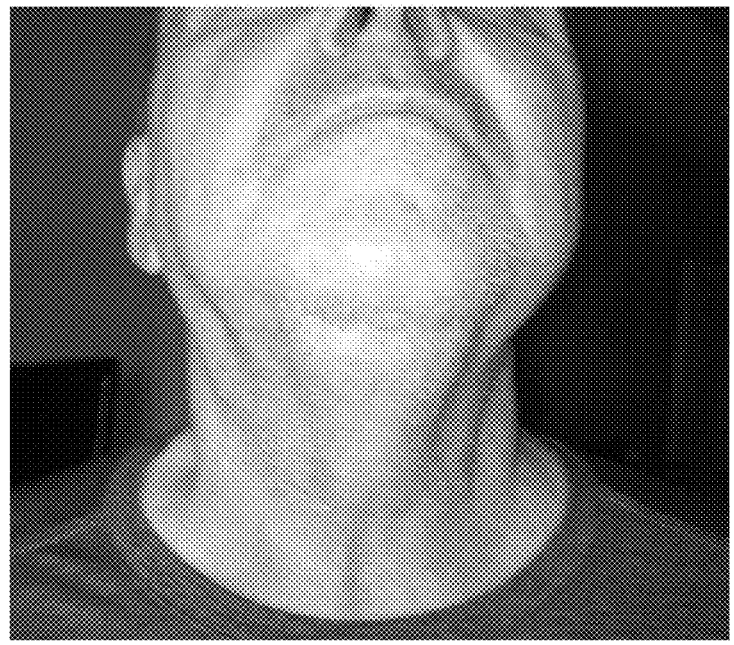
Figure 6C:
Figure 6D:
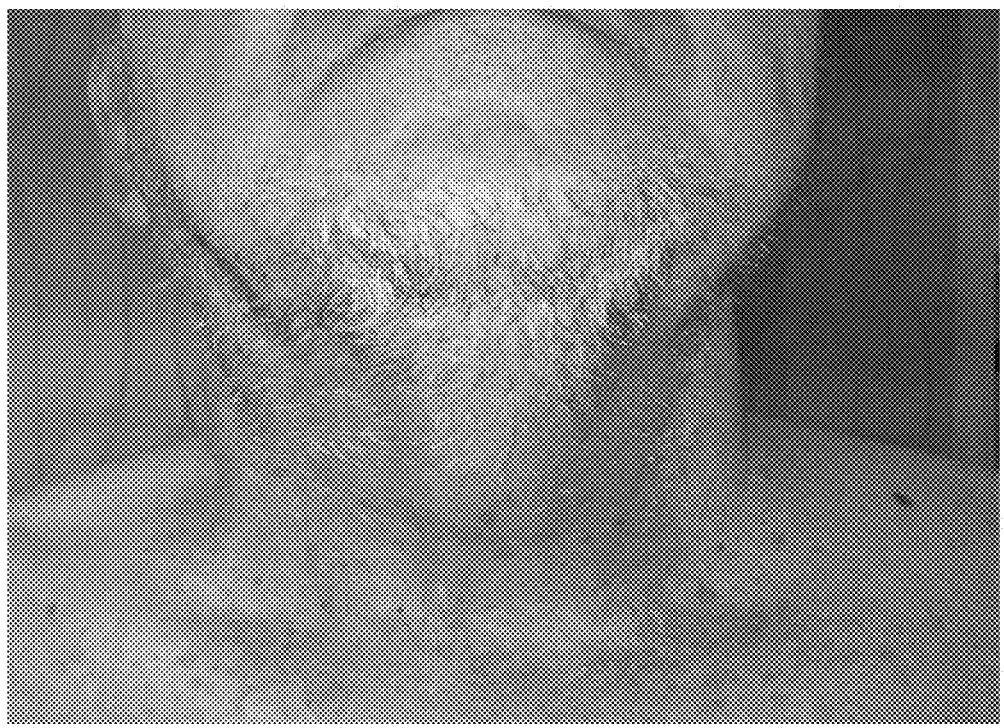
Figure 6E:
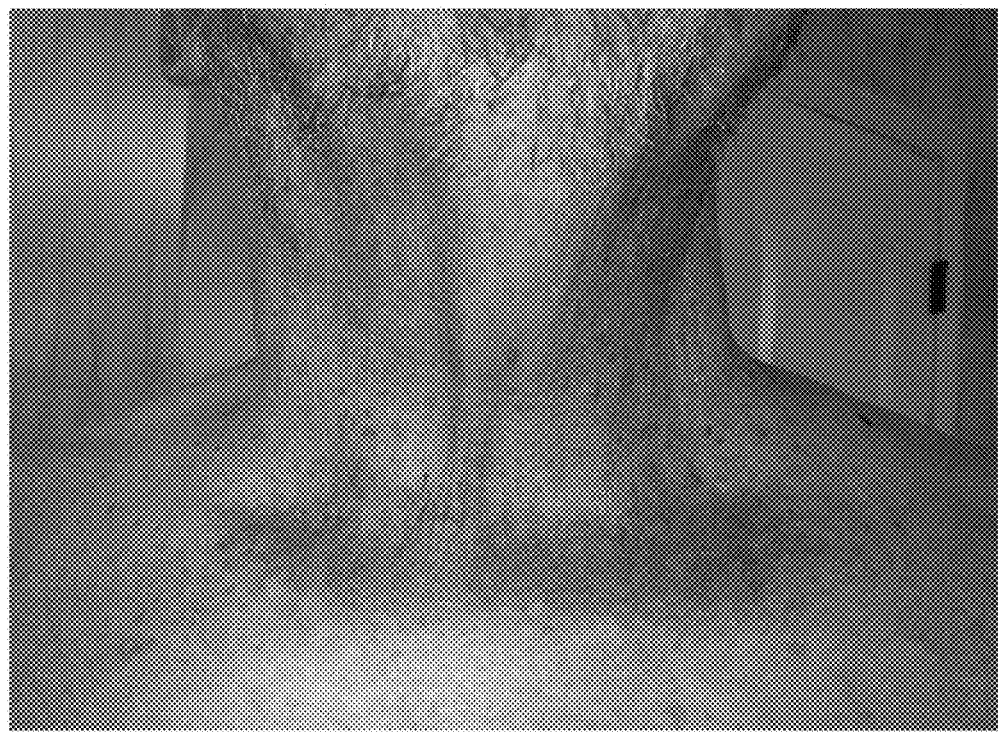
Figure 6F:

Patient C received 35 radiation treatments to the neck area as part of a treatment for adenocarcinoma of the larynx. Patient C used the compress after every treatment for 15 minutes, and then applied Aquaphor® to the cooled skin after the compress was removed. Patient C's skin turned mildly red by the end of 20 radiation treatments (FIGS. 6A-6E), but did not blister or peel. Patient C's skin began to get very red and experience some pain toward the last week of treatments (FIG. 6F), but the skin never blistered. Patient C reported no blistering after the 35 total treatments.

Patient D

Figure 7:
FIG. 7 is an image of the skin of Patient D, who received 35 radiation therapy treatments to the neck area, and who did not use any topical relief products throughout any of the radiation process. This image was taken 2 weeks post therapy showing the healing process of blisters and burning that occurred.

For comparison, FIG. 7 is an image of the skin of Patient D at the end of radiation therapy to the neck as part of a treatment for nasopharyngeal cancer, whereby the radiation oncologist aimed the beam on the neck to get to the cancer. Patient D did not use any topical relief products throughout any of the 35 radiation treatments and developed severe radiation dermatitis, as indicated by the burned and traces of blistered and peeled skin.

Any patents or publications mentioned in this specification are herein incorporated by reference to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present examples along with the methods described herein are presently representative of preferred embodiments, are exemplary, and are not intended as limitations on the scope of the disclosure. Changes therein and other uses will occur to those skilled in the art which are encompassed within the spirit of the disclosure as defined by the scope of the claims.

The invention claimed is:

1. A method of making a compress for treating and preventing radiation dermatitis, the method comprising:
   (i) mixing a solution of aloe vera, vitamin E, and lavender oil;
   (ii) storing the solution at a temperature of about 1° C. to about 4° C. for about 1 hour to about 5 hours; and
   (iii) applying the cold solution to a reservoir layer of the compress until the reservoir layer is saturated.

2. The method of claim 1, wherein the solution comprises 48 parts aloe vera, 1 part vitamin E, and 0.5 part lavender oil.

3. The method of claim 1, wherein the compress can be applied to skin exposed to radiation therapy for about 1 minute to about 60 minutes following step (iii), or stored for days, weeks, or months at a temperature of about 1° C. to about 4° C. until it is applied to skin exposed to radiation therapy.

* * * * *